(12) United States Patent
Evert et al.

(10) Patent No.: US 8,728,112 B2
(45) Date of Patent: May 20, 2014

(54) VASCULAR OCCLUSION DEVICE

(75) Inventors: Kathryn R. Evert, Bloomington, IN (US); James C. Elsesser, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 295 days.

(21) Appl. No.: 13/131,060

(22) PCT Filed: Nov. 24, 2009

(86) PCT No.: PCT/US2009/065645
§ 371 (c)(1),
(2), (4) Date: Jun. 24, 2011

(87) PCT Pub. No.: WO2010/062880
PCT Pub. Date: Jun. 3, 2010

(65) Prior Publication Data
US 2011/0257674 A1 Oct. 20, 2011

Related U.S. Application Data

(60) Provisional application No. 61/118,313, filed on Nov. 26, 2008.

(51) Int. Cl.
*A61M 29/04* (2006.01)
(52) U.S. Cl.
USPC .......................................... 606/200; 606/213
(58) Field of Classification Search
USPC .......... 606/191, 194, 200, 213–217; 128/831, 128/887
See application file for complete search history.

(56) References Cited

U.S. PATENT DOCUMENTS

| 4,619,246 | A  | * | 10/1986 | Molgaard-Nielsen et al. ............................. 128/899 |
| 5,702,421 | A  | * | 12/1997 | Schneidt ........................ 606/213 |
| 6,267,776 | B1 | * | 7/2001  | O'Connell .................... 606/200 |
| 6,368,338 | B1 | * | 4/2002  | Konya et al. ................... 606/200 |
| 7,648,713 | B2 | * | 1/2010  | Sawhney ....................... 424/426 |
| 8,235,047 | B2 | * | 8/2012  | Swann et al. ................. 128/831 |
| 2003/0229366 | A1 |   | 12/2003 | Reggie et al. |
| 2005/0137714 | A1 |   | 6/2005  | Gonzalez et al. |
| 2005/0155608 | A1 | * | 7/2005  | Pavcnik et al. ................ 128/831 |
| 2006/0009798 | A1 | * | 1/2006  | Callister et al. ............... 606/200 |
| 2007/0162103 | A1 |   | 7/2007  | Case et al. |
| 2007/0227544 | A1 | * | 10/2007 | Swann et al. .................. 128/831 |
| 2008/0312679 | A1 |   | 12/2008 | Hardert et al. |
| 2009/0062838 | A1 |   | 3/2009  | Brumleve et al. |
| 2009/0062845 | A1 |   | 3/2009  | Tekulve |

FOREIGN PATENT DOCUMENTS

WO WO 2007079407 A2 * 7/2007
WO WO 2009/124144 A1 10/2009

* cited by examiner

*Primary Examiner* — Kathleen Holwerda
(74) *Attorney, Agent, or Firm* — Brinks Gilson & Lione

(57) ABSTRACT

A vascular occlusion device for occluding a body vessel is disclosed. The device comprises a hub having proximal and distal ends and a plurality of anchoring struts. Each anchoring strut has a first end and a second end. The first ends are connected together at the hub. Each of the second ends extends freely from the first end to engage the body vessel for anchoring the device therein. The device further comprises a central strut attached to the proximal end of the hub. The device further comprises a proximal and distal members and an extracellular matrix material. The proximal and distal members are slidibly disposed about the central strut. The extracellular matrix material is disposed about the central strut between the proximal and distal members.

18 Claims, 5 Drawing Sheets

VASCULAR OCCLUSION DEVICE

CROSS-REFERENCE TO RELATED APPLICATIONS

This application claims the benefit of priority to PCT/US2009/065645 filed Nov. 26, 2008 which claims the benefit priority of U.S. Provisional Application No. 61/118,313, filed on Nov. 26, 2008, entitled "VASCULAR OCCLUSION DEVICE," the entire contents of which are incorporated herein by reference.

BACKGROUND

1. Field of Invention

The present invention relates to medical devices. More particularly, the invention relates to vascular occlusion devices and methods of occluding fluid flow through a body vessel.

2. Background of the Invention

Pushable fibered coils have been used as a primary occluding device for treatment of various arteriovenous malformations (AVM) and varicoceles, as well as for many other arteriovenous abnormalities in the body. Occluding devices are also used to repair abnormal shunts between arteries and veins, prevent or reduce blood flow to tumors, stop hemorrhaging as a result of trauma, and stabilize aneurysms to prevent rupture. Pushable fibered coils may be configured in a variety of sizes with varying diameters and may be made of several different materials including stainless steel and platinum.

Although current pushable fibered coils are adequate, such coils may be improved for more effective occlusion of fluid flow though a lumen of a body vessel. Many medical procedures for occluding blood flow through an artery or vein require a number of coils, since a single coil or two may not be sufficient to effectively occlude blood flow through a lumen of an artery or vein. In many current procedures, many coils may be packed within each other to produce effective cross sectional occlusion of fluid flow through a body vessel. In some instances, these procedures may involve an undesirable amount of additional time and costs.

Moreover, the use of a number of coils to occlude a body vessel is also undesirable in many circumstances, since medical practitioners have been challenged with coil migration after deployment thereof.

SUMMARY

The present invention provides a vascular occlusion device and a method of occluding fluid flow through a lumen of a body vessel. The device eliminates the need to use a number of coils, thereby saving time and costs along with reducing the chance of migration.

In one embodiment, the present invention provides a vascular occlusion device for occluding a body vessel. The device comprises a hub having proximal and distal ends and a plurality of anchoring struts. Each anchoring strut has a first end and a second end. The first ends are connected together at the hub. Each of the second ends extends freely from the first end to engage the body vessel for anchoring the device therein. The device further comprises a central strut attached to the proximal end of the hub. The device further comprises proximal and distal members and an extracellular matrix material. The proximal and distal members are slidibly disposed about the central strut. The extracellular matrix material is disposed about the central strut between the proximal and distal members.

Another embodiment, the present invention provides a vascular occlusion device comprising a hub having proximal and distal ends and a plurality of anchoring struts. Each anchoring strut has a first end and a second end. The first ends are connected to the hub and each of the second ends extends freely from the first end to engage the body vessel for anchoring the device therein. The device further comprises a central strut detachably connected to the proximal end of the hub and an extracellular matrix material disposed about the central strut and formed on a portion of the plurality of struts.

In another example, the present invention provides a method of occluding a body vessel. The method comprises introducing the vascular occlusion device through a delivery catheter. The method further includes pushing the anchoring struts through the catheter to engage the body vessel for anchoring the device therein and absorbing fluid in the extracellular matrix material to occlude the body vessel.

Further objects, features, and advantages of the present invention will become apparent from consideration of the following description and the appended claims when taken in connection with the accompanying drawings.

DETAILED DESCRIPTION

Embodiments of the present invention generally provide a vascular occlusion device used for transcatheter embolization. The device is preferably used to occlude fluid flow through a lumen of a body vessel such as for an occlusion of an arteriovenous malformation (AVM). In one embodiment, the device comprises a hub having proximal and distal ends and a plurality of anchoring struts, each of which connect at the distal end of the hub and extends freely there from to engage the body vessel for anchoring the device. The device further comprises a central strut attached to the proximal end of the hub and an extracellular matrix material disposed about the central strut for occluding the body vessel.

Figure 1:
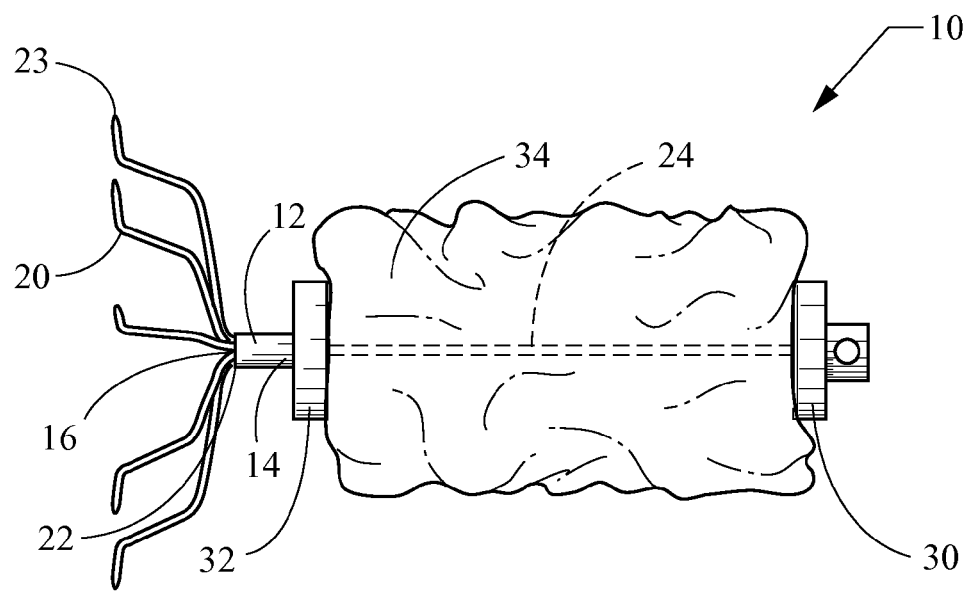
FIG. 1 is a side view of a vascular occlusion device for occluding a body vessel in accordance with one embodiment of the present invention.
Figure 2:
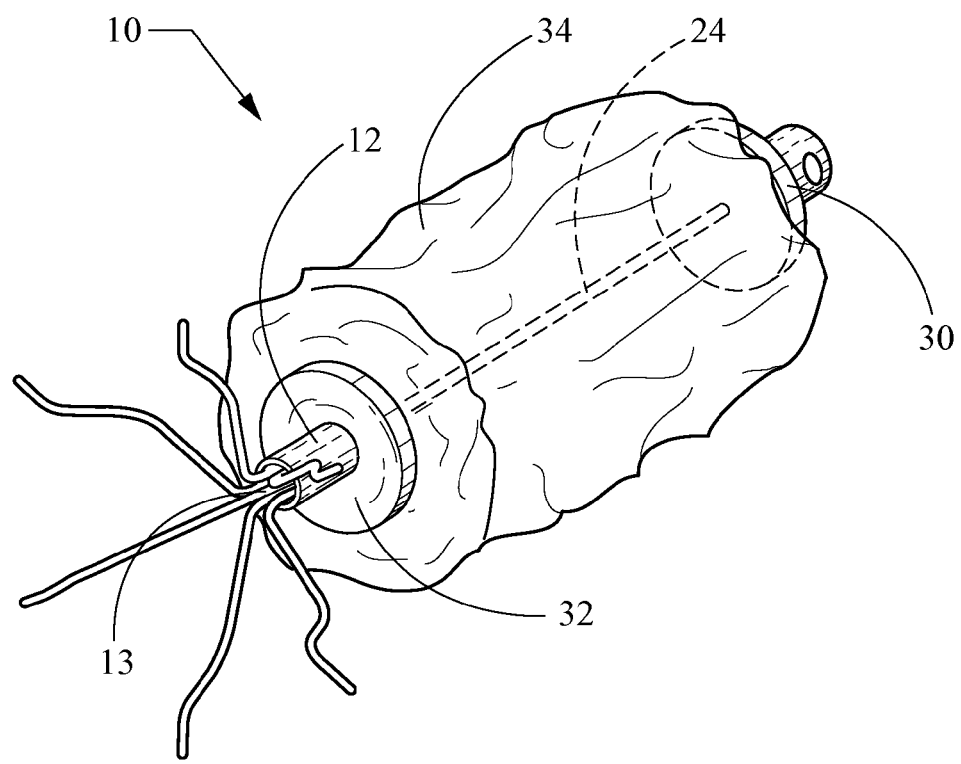
FIG. 2 is a prospective view of the occlusion device in FIG. 1.

FIGS. 1 and 2 illustrate a vascular occlusion device 10 for occluding a body vessel in accordance with one embodiment of the present invention. As shown, the device 10 comprises a hub 12 having a proximal end 14 and a distal end 16. Preferably, the hub 12 is a collar that comprises a bore 13 formed therethrough. In this embodiment, a plurality of anchoring struts 20 is attached to the hub 12 and extends therefrom. More specifically, each anchoring strut has a first end 22 and a second end 23, wherein each anchoring strut extends arcuately from the first end 22 to the second end 23. The first ends 22 are connected together at the distal end 16 of the hub 12. Each of the second ends 23 extends freely from the corresponding first end 22 to engage the body vessel for anchoring the device 10 when deployed in the body vessel. In this embodiment, the device 10 further comprises a central strut 24 attached to the proximal end 14 of the hub 12. In this embodiment, the central strut 24 is attached to the proximal end 14 of the hub 12 by being disposed in the bore 13. The central strut 24 may be attached to the hub 12 by interference fit, soldering, sonic welding, or any other suitable means. The central strut 24 is preferably made of shape memory alloy, such as Nitinol.

Figure 3:
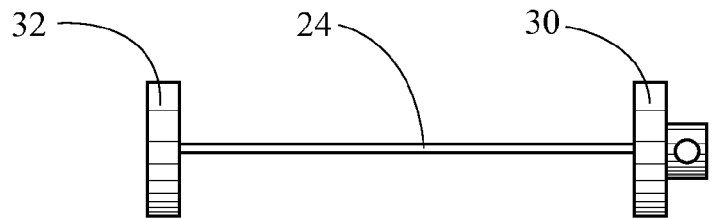
FIG. 3 is a side view of a proximal and distal members of the vascular occlusion device of FIG. 1.
Figure 4:
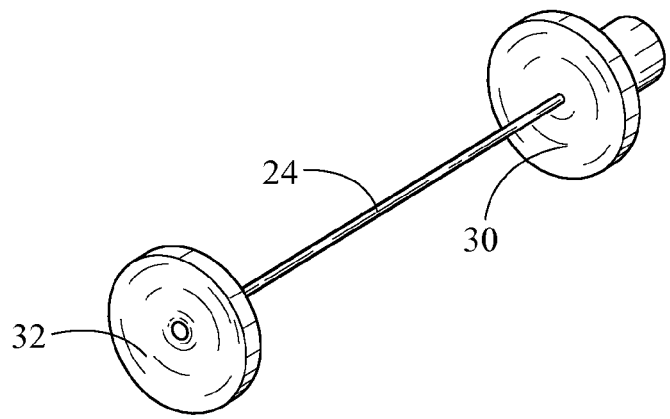
FIG. 4 is a prospective view of proximal and distal members and FIG. 3.

As shown in FIGS. 2-4, the device 10 further comprises a proximal member 30 and a distal member 32, each of which is slidibly disposed about the central strut 24. Preferably, the distal member 32 is disposed adjacent the hub 12. In this embodiment, the proximal and distal members 30,32 are proximal and distal discs having a circular configuration, respectively. Preferably, the proximal and distal members 30,32 are made of any bio-compatible suitable material such as silicone. Moreover, the proximal member 30 includes an attachment configuration so that a deployment apparatus may be used to facilitate introduction and deployment of the device 10. In this example, proximal member 30 includes a hole formed therethrough for attachment and release of a deployment apparatus.

As shown in FIGS. 1 and 2, the device 10 further comprises extracellular matrix (ECM) material 34 disposed about the central strut 24 between the proximal and distal members 32. In use, the proximal and distal members 30,32 provide enhanced stability to the ECM material 34 to prevent the EMC material from migration. The extracellular matrix material 34 may comprise small intestine submucosa, Dacron weave, and a hydrogel. In another embodiment the extracellular matrix material 34 may comprise an extracellular matrix material 34 with one or more alkaline substances. In use, the ECM material 34 occludes fluid or blood flow through a body vessel.

In additional embodiments, occlusion devices of the invention can be made from other ECMs or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner. Illustratively, the expanded material can be enriched with bioactive components, dried, and/or molded, etc., in the formation of for example a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a bodily segment within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. (Celsius). In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material.

A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of three-dimensionally stable shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

Figure 5:
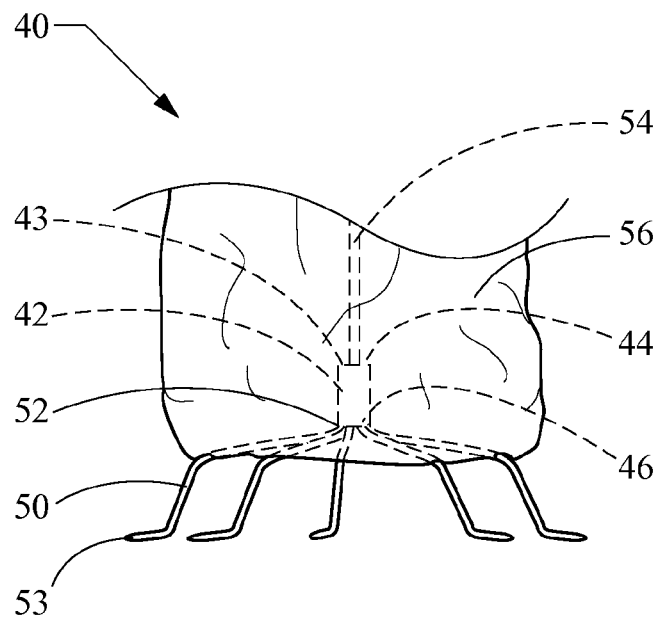
FIG. 5 is a side view of a vascular occlusion device for occluding a body vessel in accordance with another embodiment of the present invention.

FIG. 5 illustrates a vascular occlusion device 40 for occluding a body vessel in accordance with another embodiment of the present invention. As shown, the device 40 comprises similar components as the device 10 described above. For example, the device 40 comprises a hub 42, a proximal end 44, a distal end 46, a plurality of anchoring struts 50, first ends 52, and second ends 53 similar to the hub 12, the proximal end 14, the distal end 16, the plurality of anchoring struts 20, the first ends 22, and the second ends 23 of device 10 above.

However, in this embodiment, the device 40 comprises a central strut 54 that is detachably connected to the proximal end 44 of the hub 42 by way of the bore 43. The central strut 54 may be configured to be detachably connected to the proximal end 44 of the hub 42 by any suitable means. For example, the central strut 54 and the hub 42 may have cooperating or mating threads formed thereon or a mechanism to release the central strut 54 from the hub 42. Moreover, as shown without proximal and distal members, the ECM material 56 is disposed about the central strut 54 and formed on at least a portion of the plurality of anchoring struts 50. The central strut 54 is disposed and runs through the ECM material 56 to provide structure so that the ECM material 56 does not migrate. In use, as the central strut 54 is detached from the hub 42, the central strut 54 is slidably removed from the ECM material 56 which will remain disposed on the plurality of anchoring struts 50 and in contact with the hub 42. Thus, in use, the ECM material 56 maintains enough structure so that the ECM material 56 does not migrate after detachment from the central strut 54. In both embodiments mentioned above, the length of the central strut is determined by the desired size of the ECM material that is used for the given procedure.

Figure 6:
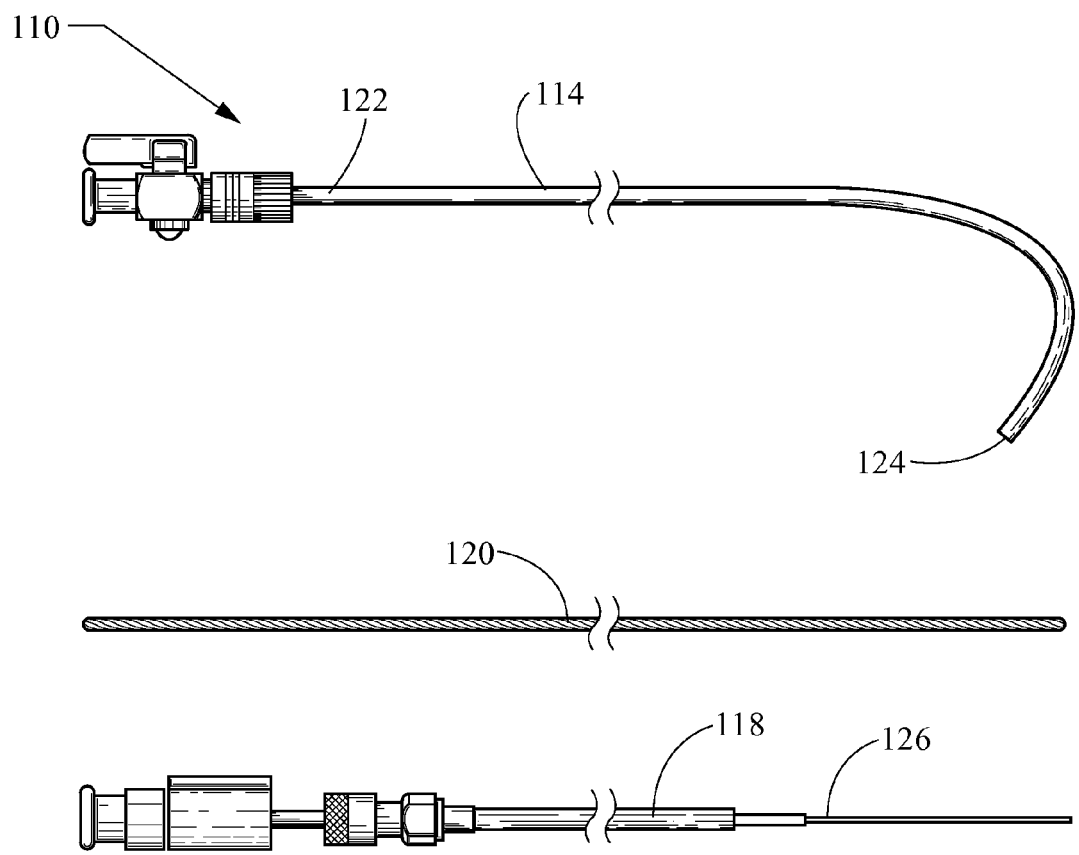
FIG. 6 is an exploded view of an embolization kit for deploying a vascular occlusion device in accordance with one embodiment of the present invention.
Figure 7:
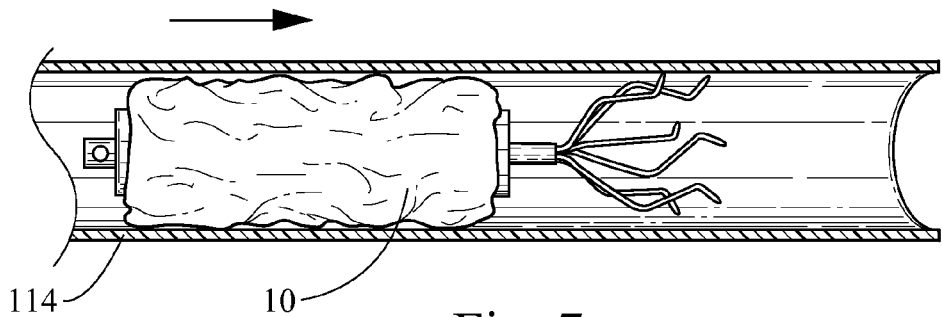
FIG. 7 is an environmental view of the vascular occlusion device preloaded in a deployment assembly.

FIG. 6 depicts a body vessel embolization kit 110 which implements the device in accordance with one embodiment of the present invention. As shown, the kit 110 includes a microcatheter 114 defining a catheter lumen and preferably made from a soft, flexible material such as silicone or any other suitable material. Generally, the microcatheter 114 has a proximal end 122, a distal end 124, and a plastic adapter or hub to receive apparatus to be advanced therethrough. In this embodiment, the inside diameter of the microcatheter may range preferably between about 0.010 and 0.030 inch, more preferably between about 0.014 and 0.027 inch. FIG. 7 illustrates a vascular occlusion device loaded in a delivery catheter similar to microcatheter 114 of FIG. 6 for delivery into a body vessel of a patient. In this embodiment, the kit 110 further includes a guide wire 120 which provides a path during insertion of the kit within a body vessel. The size of the wire guide is based on the inside diameter of the guide catheter.

In this embodiment, the kit 110 further includes a polytetrafluoroethylene (PTFE) guide catheter or sheath 118 for percutaneously introducing the microcatheter 114 in a body vessel. Of course, any other suitable material may be used without falling beyond the scope or spirit of the present invention. The guide catheter 118 may have a size of about 2-French to 8-French and allows the microcatheter 114 to be inserted therethrough to a desired location in the body vessel. The guide catheter 118 receives the microcatheter 114 and provides stability of the microcatheter 114 at a desired location of the body vessel. For example, the guide catheter 118 may stay stationary within a common visceral artery, e.g., a common hepatic artery, and add stability to the microcatheter 114 as the microcatheter is advanced through the guide catheter to a point of occlusion in a connecting artery, e.g., the left or right hepatic artery.

When the distal end 124 of the microcatheter 114 is at the point of occlusion in the body vessel, the device is loaded at the proximal end 122 of the microcatheter 114 and is advanced through the microcatheter for deployment through the distal end 124. In one embodiment, a push wire 126 may be used to mechanically advance or push the device through the microcatheter 114. The size of the push wire used depends on the diameter of the microcatheter.

It is to be understood that the body vessel embolization kit 110 described above is merely one example of a kit that may be used to deploy the occluding device in a body vessel. Of course, other kits, assemblies, and systems may be used to deploy any embodiment of the device without falling beyond the scope or spirit of the present invention.

Figure 8A:
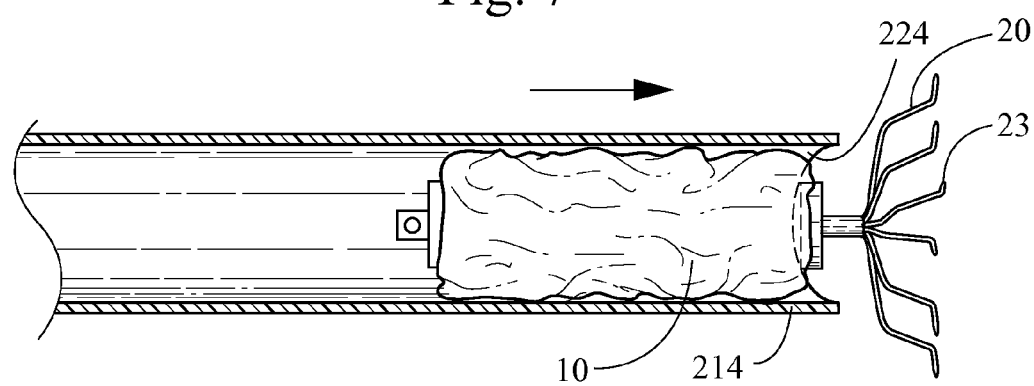
FIGS. 8*a*-8*c* are side views of deployment steps during delivery of the vascular inclusion device.
Figure 8B:
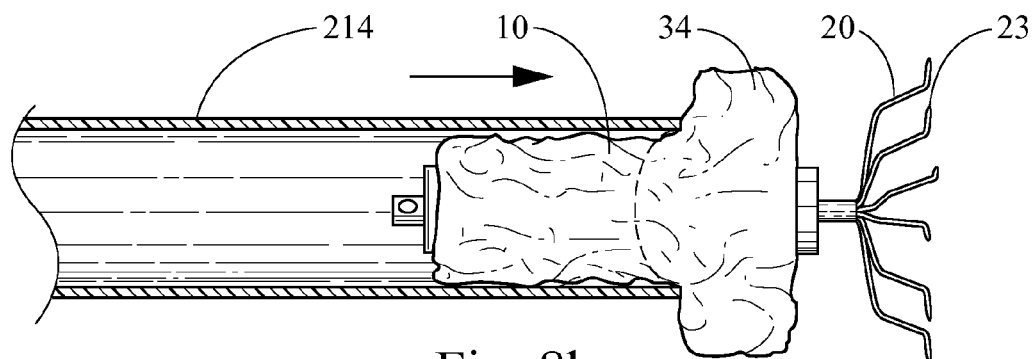
Figure 8C:
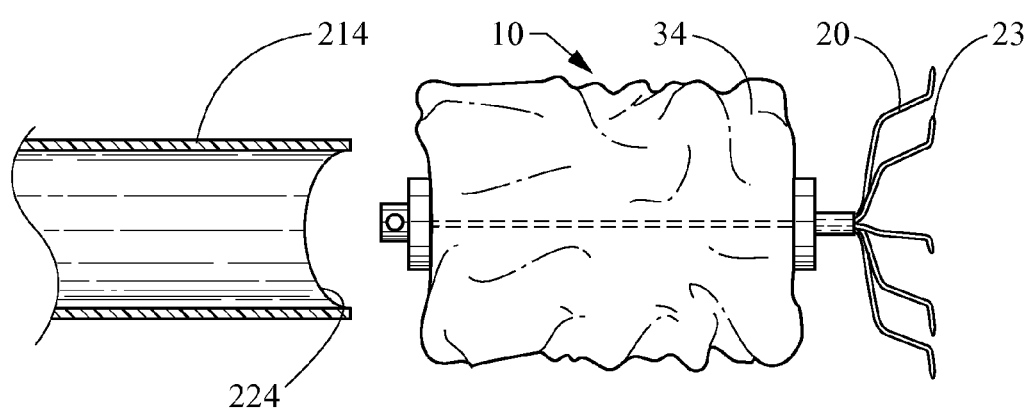

In FIG. 8a, the device 10 is partially deployed in a body vessel. FIG. 8a shows the device 10 being delivered by a delivery catheter 214 though the vasculature of a patient. When the distal end 224 of the catheter 214 is at the point of occlusion in the body vessel, the device 10 if not already preloaded is loaded at its proximal end and is advanced through the catheter 214 for deployment through the distal end 224. In one embodiment, a push wire may be used to mechanically advance or push the device 10 through the catheter 214. In FIG. 8b, the device 10 is further but still partially deployed in the body vessel. As shown, the ECM 34 material is partially deployed. Fluoroscopy may be used to assess the accuracy of deployment. If needed, the device 10 may be retracted and repositioned. In FIG. 8c, the device 10 is fully deployed in the body vessel. Deployment is completed after an assessment has been made, e.g., via fluoroscopy, as to the accuracy of the position of the device.

Figure 9:
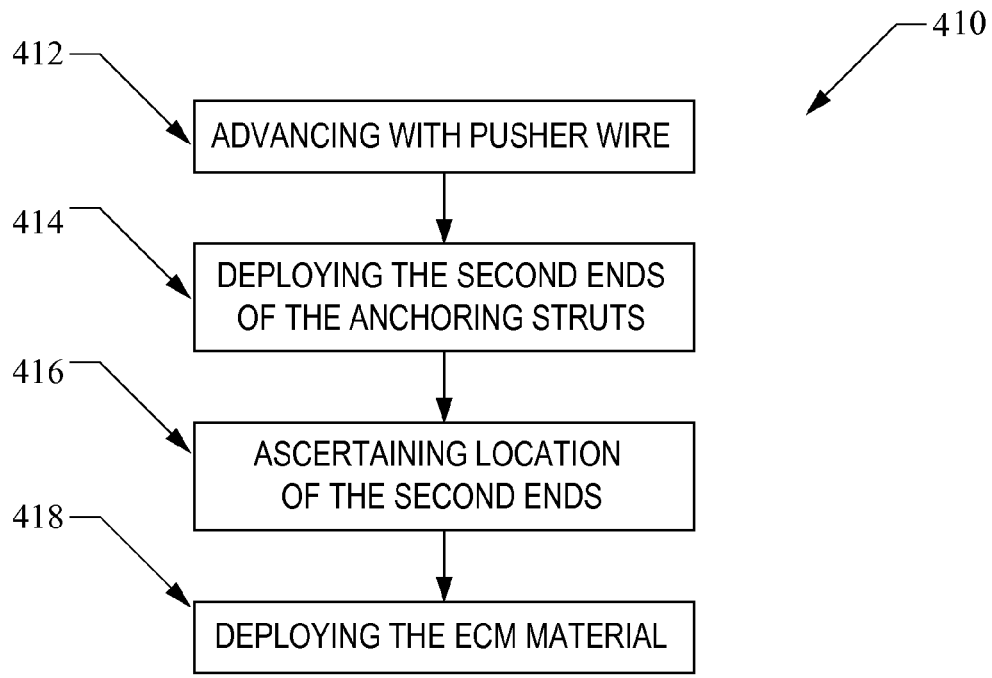
FIG. 9 is a flowchart depicting one method of occluding a body vessel in accordance with one example of the present invention.

The device may be deployed in a body vessel by any suitable manner, such as by a push embolization method, a squirt embolization method, or via a deployment apparatus. In accordance with one example of the present invention, FIG. 9 illustrates a push embolization method 410 of transcatheter embolization using an embodiment of the device 10 mentioned above. As typically performed in embolotherapy, an introducer or a guide catheter is percutaneously introduced into the body vessel of a patient and a microcatheter is passed through the guide catheter to position the microcatheter at a desired point of occlusion in the body vessel.

The device, which is preloaded within the kit (see FIG. 7), is loaded in the hub at the proximal end of the microcatheter. In step 412, the device is advanced by the pusher wire in accordance with this method of deploying the device.

In step 414, the second ends of the anchoring struts are deployed at the desired point of occlusion in the body vessel as the ECM material is held in the microcatheter (see FIGS. 8a and 8b). In step 416, the location of the second ends in the body vessel is ascertained by any suitable means, such as by fluoroscopy, relative to the body vessel. If the second ends are at the desired point of occlusion in the body vessel, then the ECM is deployed in the body vessel in step 418 (see FIG. 8c).

However, if it is ascertained in step 416 that the second ends of the device are not at the desired point of occlusion, then the position of the microcatheter is moved fore or aft relative to the body vessel such that the second ends are placed at the desired point of occlusion. As the device is then fully deployed in the body vessel, flow is blocked to occlude the body vessel.

Figure 10:
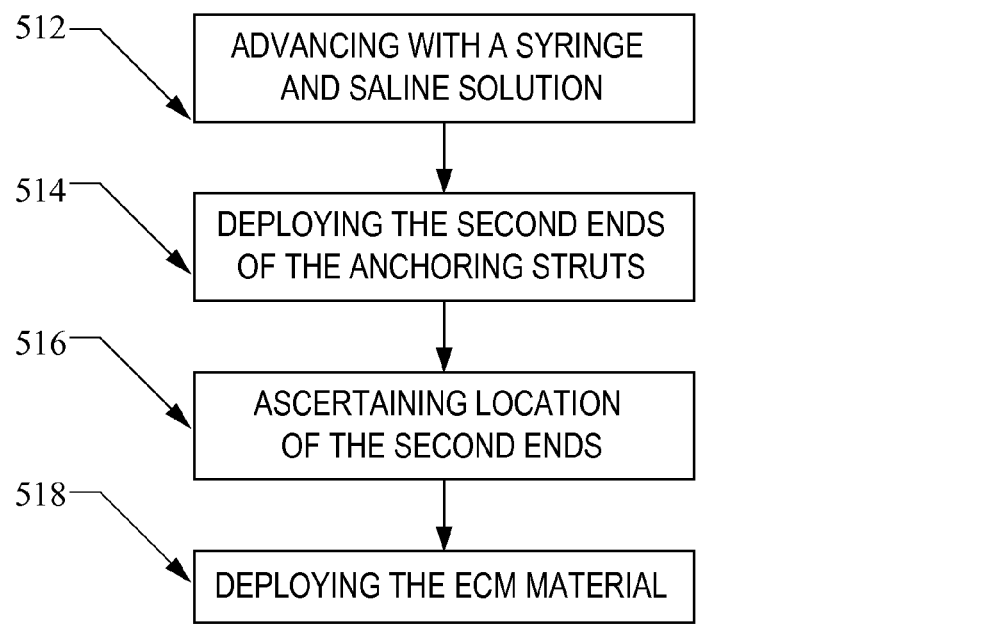
FIG. 10 is a flowchart depicting another method of occluding a body vessel.

FIG. 10 illustrates a squirt embolization method 510 of transcatheter embolization using an embodiment of the device of the present invention. As typically performed in embolotherapy, a guide catheter is introduced into the body vessel as described above in the push embolization method. Once the microcatheter is passed through the guide catheter and the device is loaded at the hub of the microcatheter, the occluding device is advanced in step 512 through the microcatheter with use of a luer lock syringe and saline solution. In step 514, the second ends of the occluding device are deployed at the desired point of occlusion in the body vessel as the ECM of the device is held in the microcatheter.

In step 516, the location of the second end in the body vessel is ascertained by any suitable means, such as by fluoroscopy, relative to the body vessel. If the second ends are at the desired point of occlusion in the body vessel, then the ECM is advanced in the body vessel with the saline solution. Thus, the ECM is deployed across the lumen of the body vessel to occlude the body vessel. FIG. 10a depicts the device 10 being deployed within a body vessel.

However, if it is ascertained in step 516 that the second ends are not at the desired point of occlusion, then the position of the microcatheter is moved fore or aft relative to the body vessel such that the second ends are is placed at the desired point of occlusion.

While the present invention has been described in terms of preferred embodiments, it will be understood, of course, that the invention is not limited thereto since modifications may be made to those skilled in the art, particularly in light of the foregoing teachings.

The invention claimed is:

1. A vascular occlusion device for occluding a body vessel, the device comprising:
    a hub having proximal and distal ends;
    a plurality of anchoring struts, each anchoring strut having a first end and a second end, the first ends being connected together at the hub, each of the second ends extending freely from the first end to engage the body vessel for anchoring the device therein;
    a central strut attached to the proximal end of the hub;
    proximal and distal members coupled to the central strut, wherein the proximal and distal members are proximal and distal discs respectively; and
    an extracellular matrix material disposed about the central strut between the proximal and distal members, wherein the extracellular matrix material has a first thickness in a compressed delivery state for delivering the extracellular matrix material to a target location and a second thickness in an expanded deployed state for occluding the body vessel, wherein the extracellular matrix material is configured to automatically expand from the first thickness of the compressed delivery state to the second thickness of the expanded deployed state.

2. The device of claim 1 wherein the hub comprises a bore formed therethrough, the central strut being attached to the proximal end of the hub and disposed in the bore.

3. The device of claim 1 wherein the central strut is made of shape memory alloy.

4. The device of claim 3 wherein the shape memory alloy is Nitinol.

5. The device of claim 1 wherein the extracellular matrix material comprises small intestine submucosa.

6. The device of claim 1 wherein the extracellular matrix material comprises an extracellular matrix material with one or more alkaline substances.

7. The device of claim 1 wherein each of the anchoring struts extend arcuately from the first end to the second end.

8. A vascular occlusion device for occluding a body vessel, the device comprising:
    a hub having proximal and distal ends;
    a plurality of anchoring struts, each anchoring strut having a first end and a second end, the first ends being connected to the hub, each of the second ends extending freely from the first end to engage the body vessel for anchoring the device therein;
    a central strut detachably connected to the proximal end of the hub; and
    an extracellular matrix material disposed about the central strut and coupled to a portion of the plurality of struts, wherein the extracellular matrix material has a first thickness in a compressed delivery state for delivering the extracellular matrix material to a target location and a second thickness in an expanded deployed state for occluding the body vessel, wherein the extracellular matrix material is configured to automatically expand from the first thickness of the compressed delivery state to the second thickness of the expanded deployed state.

9. The device of claim 8 wherein the hub comprises a bore formed therethrough, the central strut being attached to the proximal end of the hub into the bore.

10. The device of claim 8 wherein the central strut is made of shape memory alloy.

11. The device of claim 10 wherein the shape memory alloy is Nitinol.

12. The device of claim 8 wherein the extracellular matrix material comprises small intestine sub mucosa.

13. The device of claim 8 wherein the extracellular matrix material comprises an extracellular matrix material with one or more alkaline substances.

14. The device of claim 8 wherein each of the anchoring struts extend arcuately from the first end to the second end.

15. A method of occluding a body vessel, the method comprising:
    introducing a vascular occlusion device through a delivery catheter, the device comprising:
        a hub having proximal and distal ends;
        a plurality of anchoring struts, each anchoring strut having a first end and a second end, the first ends being connected together at the hub, each of the second ends extending freely from the first end to engage the body vessel for anchoring the device therein;
        a central strut attached to the proximal end of the hub;
        an extracellular matrix material disposed about the central strut, wherein the extracellular matrix material has a first thickness in a compressed delivery state for delivering the extracellular matrix material to a target location and a second thickness in an expanded deployed state for occluding the body vessel; and proximal and distal members slidably disposed about the central strut wherein the extracellular matrix is disposed between the proximal and distal members;

pushing the anchoring struts through the catheter to engage the body vessel for anchoring the device therein;

automatically radially expanding the extracellular matrix material from the first thickness of the compressed delivery state to the second thickness of the expanded deployed state; and absorbing blood in the extracellular matrix material to occlude the body vessel.

16. The method of claim 15 wherein pushing the anchoring struts comprises:

ascertaining the location of the anchoring struts in the body vessel; and deploying the device in the body vessel at a point of occlusion in the body vessel.

17. The method of claim 16 wherein ascertaining the location comprises:

repositioning the anchoring struts within the body vessel to the point of occlusion in the body vessel.

18. A vascular occlusion device for occluding a body vessel, the device comprising:

a hub having proximal and distal ends;

a plurality of anchoring struts, each anchoring strut having a first end and a second end, the first ends being connected together at the hub, each of the second ends extending freely from the first end to engage the body vessel for anchoring the device therein;

a central strut attached to the proximal end of the hub;

proximal and distal members coupled to the central strut, wherein the proximal and distal members are slidably disposed about the central strut; and an extracellular matrix material disposed about the central strut between the proximal and distal members, wherein the extracellular matrix material has a first thickness in a compressed delivery state for delivering the extracellular matrix material to a target location and a second thickness in an expanded deployed state for occluding the body vessel, wherein the extracellular matrix material is configured to automatically expand from the first thickness of the compressed delivery state to the second thickness of the expanded deployed state.

* * * * *